US012565675B2

(12) United States Patent
De Simone Molina et al.

(10) Patent No.: US 12,565,675 B2
(45) Date of Patent: Mar. 3, 2026

(54) METHOD FOR SELECTING APTAMERS WITH HIGH TARGET SPECIFICITY IN A MICROFLUIDIC DEVICE PLATFORM FOR CO-CULTURE OF MULTIPLE TISSUES

(71) Applicant: BIOPTAMERS PESQUISA E DESENVOLVIMENTO LTDA, São Paulo/SP (BR)

(72) Inventors: Erika De Simone Molina, São Paulo (BR); Emerson Galves Moretto, São Paulo/SP (BR)

(73) Assignee: BIOPTAMERS PESQUISA E DESENVOLVIMENTO LTDA, São Paulo/SP (BR)

( * ) Notice: Subject to any disclaimer, the term of this patent is extended or adjusted under 35 U.S.C. 154(b) by 754 days.

(21) Appl. No.: 17/908,712

(22) PCT Filed: Mar. 5, 2021

(86) PCT No.: PCT/BR2021/050096
§ 371 (c)(1),
(2) Date: Sep. 1, 2022

(87) PCT Pub. No.: WO2021/174327
PCT Pub. Date: Sep. 10, 2021

(65) Prior Publication Data
US 2023/0159988 A1     May 25, 2023

(30) Foreign Application Priority Data
Mar. 5, 2020    (BR) .......................... 1020200044362

(51) Int. Cl.
| C12Q 1/6811 | (2018.01) |
| B01L 3/00 | (2006.01) |
| C12M 3/00 | (2006.01) |
| C12N 5/00 | (2006.01) |
| C12N 15/115 | (2010.01) |

(52) U.S. Cl.
CPC .............. *C12Q 1/6811* (2013.01); *B01L 3/50* (2013.01); *C12M 3/00* (2013.01); *C12N 5/00* (2013.01); *C12N 15/115* (2013.01)

(58) Field of Classification Search
None
See application file for complete search history.

(56) References Cited

FOREIGN PATENT DOCUMENTS

WO      2011014674 A2      2/2011

OTHER PUBLICATIONS

Lin, C. et al., IEEE MEMS, Jan. 2020, pp. 1083-1085.*
Kaminaga, M. et al. Microfluidic Device for Screening for Target Cell-Specific Binding Molecules by Using Adherent Cells. Micromachines. 2019. vol. 10, No. 1: 41, 13 pages.
Gopinathan P. et al. Automated selection of aptamers against cholangiocarcinoma cells on an integrated microfluidic platform. Biomicrofluidics. 2017. vol. 11, No. 4, 17 pages.
Hung, L. Y. et al. Microfluidic platforms for rapid screening of cancer affinity reagents by using tissue samples. Biomicrofluidics. 2018. vol. 12, 17 pages.
Liu, W. T. et al. An automated microfluidic system for selection of aptamer probes against ovarian cancer tissues. Biomicrofluidics. 2019. vol. 13, 10 pages.

* cited by examiner

*Primary Examiner* — Michael D Burkhart
(74) *Attorney, Agent, or Firm* — Meunier Carlin & Curfman LLC

(57) ABSTRACT

This invention consists of a method for the development of personalized target anticancer therapies based on aptamers and through the systemic modeling of an individual in microfluidic devices. This invention is embodied in microfluidic devices, connections, systems, and methods for the development specific aptamers for the relevant complex biological environment targets. In a first mode, the invention provides methods for the development of target therapies which involves the maintenance of target cancerous cells in co-culture with non-target and non-cancerous cells by using microfluidic devices modularly arranged in closed systems for the development of aptamers. In a second mode, the invention provides a method for the development of target therapies, which includes the maintenance of target cells in co-culture with non-target cells by using microfluidic devices modularly arranged in closed systems. In this case, the invention provides the development of aptamers for the relevant target in homeostatic balance with the components of the fluid conditioned by the co-culture with non-target cells.

6 Claims, 2 Drawing Sheets

METHOD FOR SELECTING APTAMERS WITH HIGH TARGET SPECIFICITY IN A MICROFLUIDIC DEVICE PLATFORM FOR CO-CULTURE OF MULTIPLE TISSUES

CROSS REFERENCE TO RELATED APPLICATIONS

This application is a national stage application filed under 35 U.S.C. § 371 of PCT/BR2021/050096 filed Mar. 5, 2021, which claims priority to and benefit of Brazilian application Ser. No. 10/202,00044362 filed Mar. 5, 2020.

FIELD OF INVENTION

The invention described herein refers to the specificity of aptamers and target therapy in the field of personalized medicine. More specifically, to one or more microfluidic devices, method, components and system for cell culture and development of aptamers with greater specificity by the target of interest through the SELEX technique. In particular, it refers to the modeling of aggressive types of cancer for the development of personalized aptamers for a patient.

PRIOR ART

Cancer comprises a group of diseases that, in common, present uncontrolled cell division with the potential to spread to other parts of the body. Especially for the more aggressive types of the disease, conventional chemotherapy treatment is the main cause of the patient's survival incompatibility.

There are different types of targeted cancer therapies, grouped according to their nature and the effect they exert. Generally speaking, a targeted therapy works by targeting the differences that support the survival and growth of cancerous cells. The identification of new anticancer compounds can be done through libraries of combinatorial molecules and ligand evolution processes. In this regard, a technique known as SELEX, from Systematic Evolution of Ligands by EXponential enrichment, has been prominent in the identification and selection of molecules called aptamers.

From the Latin Aptus (bond) combined with the Greek Meros (parts), aptamers consist of synthetic molecules, that is, non-naturally occurring, that present a specific interaction against a target molecule. Strategically, through this interaction, the affinity of a combinatorial library of nucleic acids is enriched by SELEX from consecutive steps of exposure, capture and amplification of the species most capable of binding to the target of interest. In this regard, aptamers interact and have a desirable reaction on the target, in this case cancerous cells, being able to modify their functional activity or even locate, guide, position and deliver other compounds with therapeutic interest.

During the classical development of aptamers by SELEX, it is possible to introduce negative selection steps against non-targets, i.e., cell types other than those of therapeutic interest. In this case, the combinatorial library is incubated with the negative target and the aim is to discard the molecules bound to it in order to amplify the species that can be called non-ligands. Ideally, negative selection results in aptamers specific to targets of interest, with no affinity for negative targets. The degree of specificity of aptamers, however, has proved insufficient to discriminate cell populations in practice, even after the negative selection steps during SELEX.

As for the in vivo variant of SELEX, despite the gain in specificity by introducing the selection of aptamers in guinea pigs, it results in aptamers selected based on affinity for targets and non-targets distorted by the xeno-animal model.

At the opposite end, the personalization of cancer treatment has emerged as a most successful therapeutic path. Due to the uniqueness of individuals and the particular evolution of the pathology in each organism, patients diagnosed with the same type of cancer present different responses to similar treatments. Given the gain in specificity for discrimination between cell populations, such as cancerous and non-cancerous, the precision of the present innovation comprises the development of specific and personalized aptamers for each patient. For this, the present invention proposes a new selection technique, based on microfluidic devices.

BRIEF DESCRIPTION OF THE INVENTION

The present invention describes the precision in personalized target cancer therapy from the combination of bioengineering and molecular biology techniques. In particular, it materializes in microfluidics devices replicating individual systemic models of patients, thus improving the degree of specificity for identification of personalized therapeutic molecules.

The present invention provides a method for treating cancer, comprising ex vivo modeling of the patient through the culture of their cancerous and non-cancerous cells, taking into account the emergence of systemic properties for the development of personalized target therapies.

On the one hand, the invention stipulates a method for systemic modeling of the patient according to the location of cancerous cells, considering the configuration of interactions and the composition between the different cell populations in the device, allowing a scan of molecules of interest.

Furthermore, it provides a method for selecting aptamers with greater specificity and demonstrates the usefulness of the technique to target cancerous cells with greater precision and at a personalized level.

The invention also discloses a method for favoring a balance between binding affinity and constant dissociation of molecules of interest in a relevant environment, considering the competition between positive and negative targets for molecules of interest and according to the composition and connection of the different cell populations.

Finally, it results in a method to replace, reduce and refine the use of pre-clinical development models based on animal experimentation, allowing to anticipate preliminary results of efficacy, distribution and toxicity.

Other exemplary aspects and embodiments of the invention are described in the following sections and appendices.

DETAILED DESCRIPTION OF THE INVENTION

Glossary

Nucleic Acid and Oligonucleotides

Figure 1:
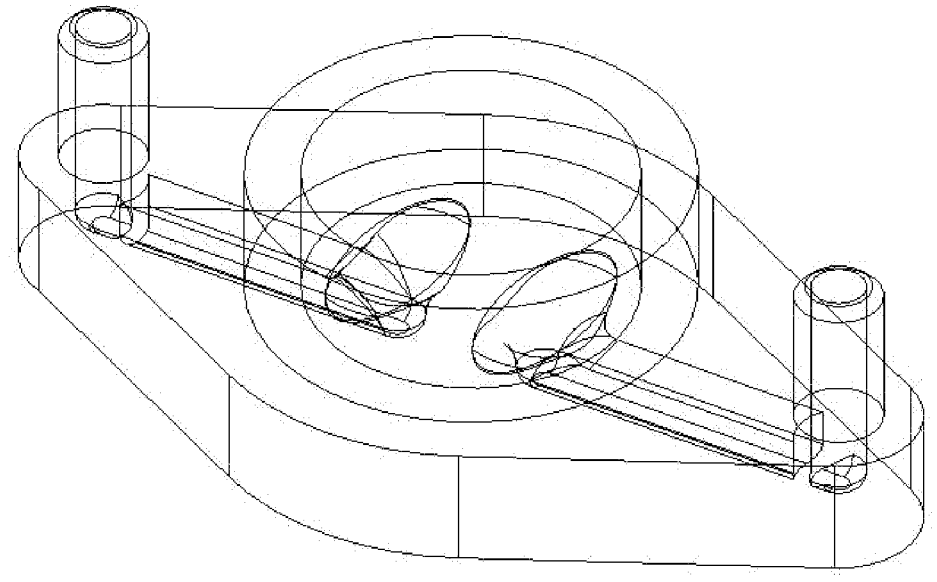
FIG. 1 illustrates the general structure of the microfluidic device according to the present invention and shows details of the substrate forming a central chamber with permeable bottom and scaffold function for isolating the target of interest.

Whenever used in this document, the terms "nucleic acids" or "oligonucleotides" mean molecules of DNA, RNA or any "XNA", understood as any oligonucleotide with chemical modification that does not prevent its copying by biochemical methods such as PCR or sequential chemical synthesis. Illustrations of these modifications are, but are not limited to: replacement of hydroxyl groups of nucleotides with halogens or methyl ether groups; use of chiral nucleotides; use of xenonucleic acids and the like.

Target

As used here, the term "target" refers to any entity with a targeting interest. To illustrate, but without limiting the scope of possibilities, a target can be: cell populations of interest, in which case the target or molecular complex can be located either on the cell surface and in internal structures; or directly an organic or inorganic molecule, but especially protein, polypeptide, lipid, lipoprotein or glycoprotein.

Aptamer

The term "aptamer" refers to non-naturally occurring nucleic acids that fold into three-dimensional structures upon which a specific interaction against the target molecule is obtained. The specific interaction of the aptamer can confer an effect, among others, of binding to the target and reaction with modification of functional activity, being able to induce activation, inhibition and facilitation of reaction between the target and other molecules.

Molecule Library

A "molecule library" mentioned throughout this document refers to sets of compounds that contain varying amounts of different chemical species. This library can present varying degrees of diversity, like combinatorial oligonucleotide libraries. The library of molecules may also have the property of randomness, in the sense that, in general, almost all the possibilities of three-dimensional configurations given by the degrees of freedom of the molecules are achieved by the ligands of the library. This library can be synthesized using various methods already known by experts in the field, or purchased commercially from third parties.

Cancer

By "cancer", the present invention, especially in its scope of application, refers to the group of diseases that in common present uncontrolled cell division with potential to form local solid tumors and metastases to other parts of the body. It also refers to neoplasms, cancerous cells and malignantly transformed cells spontaneously or from environmental factors.

Cells

As used in this document, "cells" refers to cell populations and especially, but not exclusively, explants, punctures, biopsies, primary cultures, immortalized or primary cell lines, dissociated cell culture, histotypic or even organotypic. It also refers especially, but not exclusively, to mammalian cells and which may or may not originate from a particular patient.

Non-Cancerous Cells

As used in this document, "non-cancerous cells", especially in its scope of application, refers to cells in a physiological context and not malignantly transformed, and may originate from explants, punctures, biopsies, primary cultures, immortalized cell lines or not, culture of dissociated cells, histotypic or even organotypic. It also refers especially, but not exclusively, to mammalian cells that may or may not come from a particular patient Species As used in this document, the term "species" refers to the different nucleic acid molecules that make up the combinatorial libraries used for the development of aptamers.

Explants

In the context of this document, "explants" refers to laboratory-grown mammalian tissues, which may or may not be obtained by surgically extracting a particular patient, for whom the present invention may be useful in generating aptamers against cancer. It also refers to any other animal tissue grown in a laboratory or surgically extracted.

Fluid

"Fluid" is understood to be the liquid-based circulating in the microfluidic system, which may be composed of, but not limited to, buffer solutions, culture media, blood plasma derived of human or animal origin.

Insert

By "insert", this invention refers to semi-permeable membranes for the accommodation and confinement of cell cultures without limiting communication for cell co-cultures through fluid circulation. The present invention includes a central chamber containing at the bottom a semi-permeable insert for the function of anchoring or scaffolding for the culture of cells of interest and also immobilization for the display of libraries of molecules. The chambers in this invention can have different sizes and shapes according to the designed support.

Ligand

Term "ligand" is used in the present invention to mean any chemical species with a specific three-dimensional structure capable of binding to other chemical species. Examples of ligands in the context of this invention are, but are not limited to: oligonucleotides, peptides and proteins.

Molecule

In this document, the term "molecule" expresses a set of atoms, which may be identical or different, arranged by covalent bonds. It is used as a reference to component species of substances, which can be transformed through chemical reactions generating new chemical species.

Microfluidic

"Microfluidic" and its grammatical derivatives, when used to describe the present invention, refer to the technique well known to those experts in the field that uses devices and tools to precisely control, in an orchestrated and planned manner, the flow paths of a fluid, the proportions of the composition of solutions and their combinations in association or not with any process or physical and/or chemical analysis, working on pico, nano, micro or milliliter scales.

Non-Target or Negative Target

As also used here, the term "non-target" or "negative target" refers to the opposite description of "target", that is, what is not intended to establish interactions between species. A negative target is used to remove ligand species that have the undesirable function of interacting with species other than targets.

Appropriate Period

As used in this document, the term "appropriate period" and its linguistic variations refer to any specific time interval necessary to reach the objective of the process. These periods may already be known, as described in this document, or they may be determined according to the need to achieve a satisfactory result within what is expected in some specific application situation within the scope of this invention.

SELEX

Derived from the English acronym for Systematic Evolution of Ligands by EXponential enrichment, the term SELEX is used in reference to the technique involving in vitro evolution experiments from combinatorial libraries.

Substrate

By "substrate", this document refers to the material constituting the microfluidic device, which may be, but is not limited to: liquid crystal polymer, polydimethylsiloxane, polystyrene, low temperature co-burned ceramic, additive manufacturing of photopolymerization and 3D printing.

Methods

The invention presented here is materialized in microfluidic devices, systems, components and methods used as a platform for the development of aptamers with improvement of the degree of molecular specificity to the target of interest. On the one hand, one or more methods are provided as tools to improve the selection of aptamers with specificity for relevant application in biologically complex environments. On the other hand, the method can be applied especially, but not limited to, interactive processes of sorting compounds, such as, for example, the SELEX technique for aptamers development.

According to the invention presented here, the stipulation encompasses:

a) A substrate that forms channels connecting an inlet opening and an outlet opening;

b) A substrate that forms a chamber with permeable bottom and a scaffold function for cell cultures;

c) A combination of the substrates that form the microfluidics device unit;

d) A modeling of the organism arranged through the modular combination of the device units in closed system;

e) An apparatus for guiding the circulatory flow of fluid according to the positive and negative targets of interest to be targeted;

f) A platform for maintaining the modular arrangements with temperature, pressure and pH compatible with physiological ones;

g) A platform that allows the exposure of libraries of molecules in a complex biological environment.

In the present invention, the substrate of the device is made up of layers of different materials, which are kept connected by different physico-chemical treatments, as represented in FIG. 1. When distinct materials such as glass, silicone-based organic polymer (PDMS), light-curing resin, co-burned ceramic devices (LTCC) or polystyrene (PS) are used, they are combined by joining the layers of each material through plasma exposure, followed immediately by appropriate contact, pressing each layer against each other for a certain period of time. In another technical aspect, light in the broad ultraviolet (UV) spectrum is used for the polymerization of the device when constructed using light curing resin through the 3D printing technique. The device can even have its channels coated in hydrophobic solutions when produced by 3D printing using light-curing resin. Regarding the microfluidic channels, when printed with light-curing resin, they are treated with isopropyl alcohol for a good leveling of the surface. When constructed using LTCC layers, channels are washed with varying EDTA concentrations.

Another improvement for the appropriate functioning of the device in order to minimize the leakage of fluids during its operation, especially in the connections between the insert and the device, consists in the use of a sealing ring or of silicone polymer with a diameter of 10 mm and 1.7 mm thickness properly inserted into the support slot. The size of the sealing ring is not limited to that described above, but may vary according to the possibilities within the scope of the invention described here, mainly depending on the technical specifications of the insert, which may vary. The insert slot is made exclusively of 3D printed light-curing resin and comprises a niche that accommodates the sealing ring so that the device and insert are connected.

In the present invention, the microfluidic device includes a central chamber containing at the bottom a semi-permeable insert with function of confinement or scaffold for the culture of cells of interest. In addition, the insert is also used for target immobilization in the context of exposing libraries of molecules for aptamer selection. The chambers in this invention can have different sizes and shapes and according to the designed insert support, with diameters that can vary from 4 to 120 mm and depths from 3 to 30 m or stipulated according to the standard size of wells for cell culture in laboratory dishes. In the present invention, accessory supports anchor the semi-permeable inserts to accommodate the cell culture, and the inserts can be made of polyethylene terephthalate, polycarbonate or other biologically inert material and the pores of the inserts can vary from 1 to 8 μM.

Figure 2:
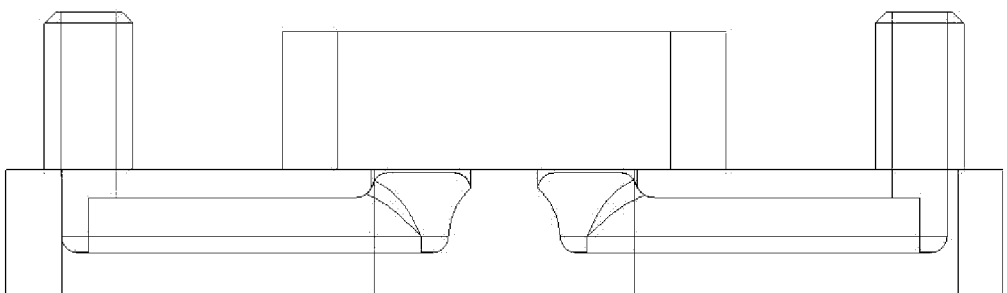
FIG. 2 illustrates the layers of materials composing the substrate and shows details of the channels of the central chamber for connecting an inlet and an outlet.

As represented in FIG. 2, illustrating the substrate composed of the layers of materials, and channels of the central chamber for connecting an inlet and an outlet. The intersection between the channels and the central chamber is formed in order to direct the fluid from the device to the interior of the chamber through the semi-permeable insert accommodated in the lower part, ensuring that the channel fluid makes a continuous flow to fill the chambers. Different channel diameters can be used to reach a desirable flow rate and local pressure according to the particular needs of the cell culture of interest, and the device can adequately accommodate these variations while maintaining the same flow by locally changing the caliber of the channel that precedes each chamber, whose inner circular sections can vary from 0.4 to 1.5 mm$^2$.

Figure 3:
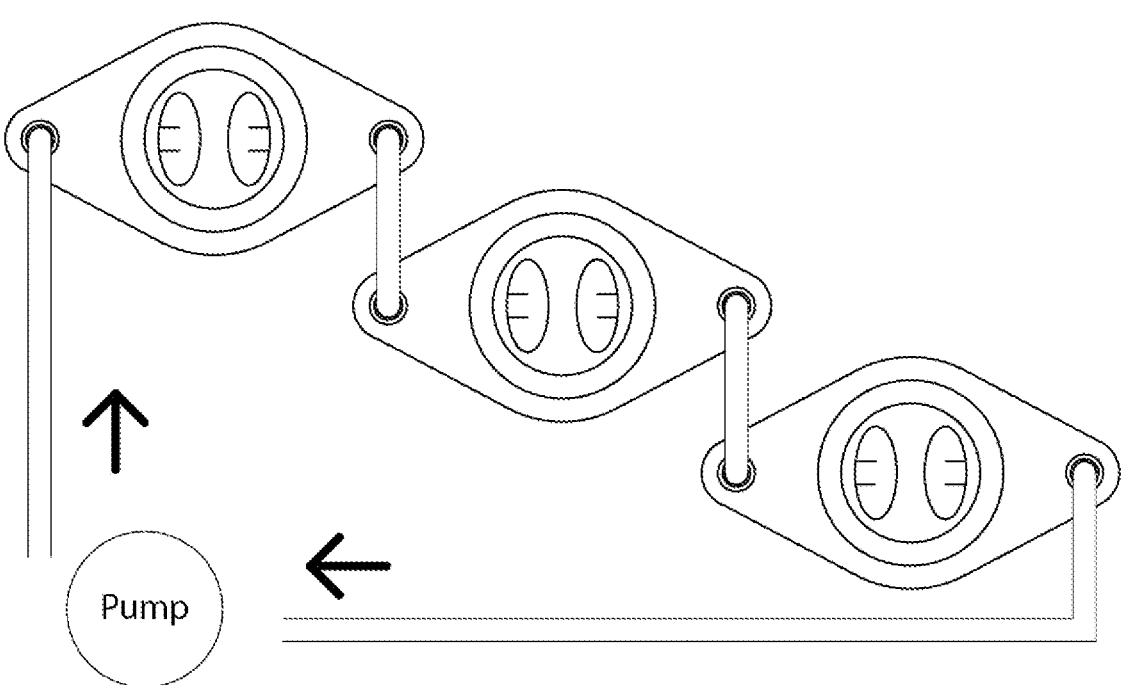
FIG. 3 illustrates an example of a combination of devices for systemic modeling of patients from connections between cell cultures and indicates the flow operation in the device controlled by a peristaltic pump.

The platform comprises devices connected by silicone tubes fixed through the protrusions on the surface of the devices in configuration where the outlet opening of a device connects with the inlet opening of at least one other device and a peristaltic pump. The devices are modularly arranged in a closed system to guide the circulatory flow with the aid of the pump, so that the fluid is continuously pushed for circulation between the devices as represented in FIG. 3. The target cells confined in the central chamber of the device are co-cultured with other non-target cells, that is, the devices are kept connected in a closed system to exchange signaling molecules through a circulating fluid, that is, in addition fluid components, cultures are exposed to signaling molecules secreted by themselves or by other cells in the system conditioning the fluid media. The fluid used in the microfluidic device may be, but not restricted to, buffer solutions such as phosphate saline solution, Hanks balanced salt solution, HEPES; cell culture media such as MEM, DMEM, F-12, RPMI adjusted to pH 7. The fluid can be composed of defined medium supplemented with growth factors or supplemented with fetal bovine serum or patient serum concentrates. The microfluidic system of the present invention includes a pump with peristaltic motion to control the flow through the devices, which flow can vary between 0.5 mL/min and 3 mL/min continuously or for programmed periods of 5 to 180 min.

Figure 4:
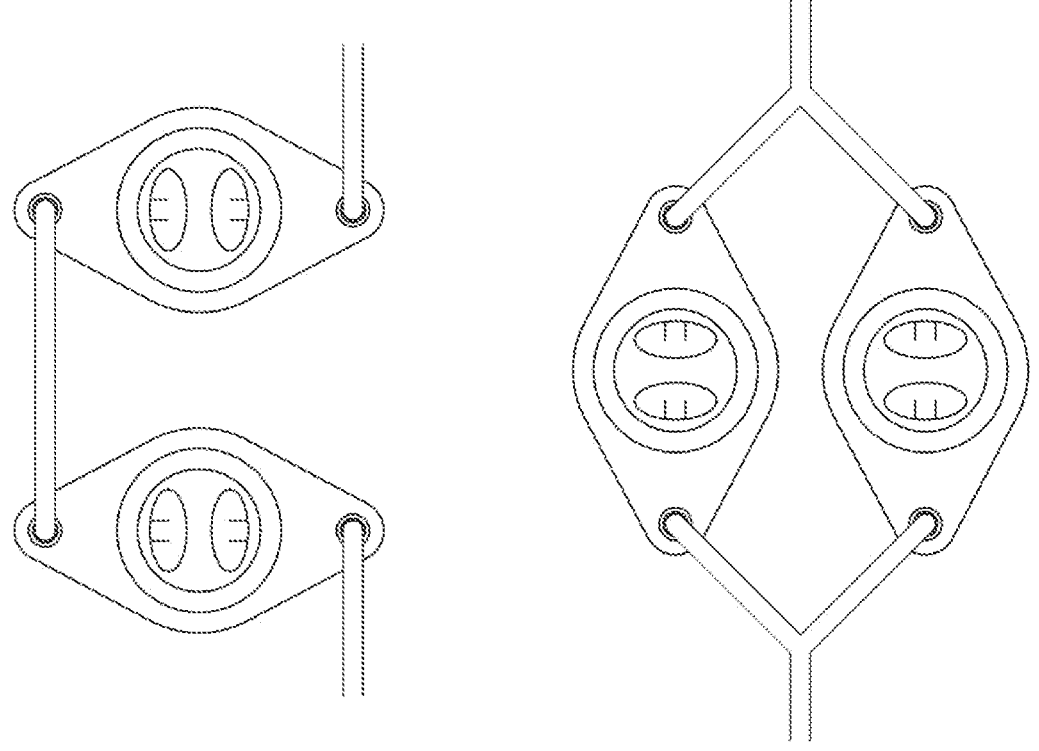
FIG. 4 illustrates connections of the combined devices in series and in parallel.

According to the in-situ location in the organism of the positive targets to be targeted, devices with cell culture of interest are arranged in combination with negative targets through serial and/or parallel connections, as shown in FIG. 4. Different combinations can be used in order to recapitulate the disposition of cells of interest in reference to blood circulation flows in the individual. In a broad sense, the inventive method provides for the modeling of patients as an external closed system, where devices are arranged in different combinations for each specific individual without the need to manufacture a new specific device. For example, but not limited to this example, for the development of target therapy against pancreatic tumor, the flow of the device must go through a device 1 with lung cell culture, then split into two devices connected in parallel, one being device 3 containing cultures of pancreatic cancerous cells and another device 4 containing cultures of peritumoral cells or non-malignantly transformed pancreas cells. The flows are pooled and proceed to a device 5 containing liver cell cultures and then directed to a device 6 containing bone marrow cultures. Finally, the flow is directed to a peristaltic pump and again directed to device 1.

For all the ways in which devices can be arranged to organize positive and negative targets, the cell cultures of interest must be confined for mobilization of the fluid components, including the molecules derived from the combinatorial library for aptamer selection and recovery of the ligand-binding species. For platform operation, the fluid is at a temperature of 37° C., humid atmosphere and with 5% $CO_2$ during circulation through the arrangement of devices. After an appropriate period to equalize the association and dissociation rates of the fluid components circulating through the targets and establishment of a homeostatic balance between the positive and negative targets, the combinatorial library of nucleic acids is introduced for the selection of aptamers through the reference technique SELEX. The library of molecules can be exemplified by an application of this invention to aptamer selection through SELEX. The Nucleic acid library can be produced by sequential chemical synthesis and/or by enzymatic reactions, being composed of about $10^9$ to $10^{15}$ random oligonucleotides. Such oligonucleotides contain 70 to 100 nucleotides and present a central random region flanked by conserved regions for primer hybridization and polymerase chain reaction amplification.

After a period of exposure of the nucleic acid library, the target cell culture is collected for extraction of ligand molecules. Adhered ligands can be highlighted by procedures that change the three-dimensional structure of the ligand, such as temperature (70-95° C.), high concentrations of salts (such as KCl, NaCl, MgCl2, etc.), changes in pH by treatment with acidic or basic solution, denaturing agents such as urea, ethidium bromide, phenol-chloroform method or by chemical bonding competition (with high concentrations of imidazole, glutathione, or known-target monoclonal antibodies). The recovered molecules are amplified by polymerase chain reactions and reconstituted in their single-stranded form, and can then either be subjected to a subsequent cycle of selection or proceed to the identification of aptamers. As some cycles are performed, a greater number of copies of the ligands presenting greater affinity tends to be enriched by binding competition, being necessary in the proposed invention from 3 to 8 cycles to obtain aptamers. Through the present invention, the method materialized in the platform implies a new technical effect to the SELEX technique, providing specificity for the application of aptamers in biologically complex and relevant environments such as, for example, but not limited to, personalized target cancer therapy. In contrast, the application of the SELEX technique against respective positive and negative targets disconnected from a homeostatic equilibrium does not result in a satisfactory level of specificity for therapeutic applications.

According to the present invention, it is suggested that the specificity of the developed aptamer simulates the degree obtained through the SELEX technique in vivo in animal guinea pigs, with the advantage of parallel providing targets and environment derived from the patient himself for therapeutic purposes.

The invention described here stipulates a method for selecting aptamers with high specificity by target cells:

a) In the device substrate, fix a support in the central chamber containing the appropriate porosity insert for the confinement of the cell types of interest;

b) Arrange the devices modularly in a closed system through combination connections in series and/or in parallel through the coupling of the protuberances of the substrate to the connectors and to the silicone tubes;

c) Fill the system of channels and chambers of the devices with fluid at 37° C.;

d) Accommodating the cell cultures of interest in the respective central chambers of the devices;

e) Circulate the fluid in the system for an adequate period, which may vary between 10 and 72 hours;

f) Injecting a combinatorial library of molecules into the system for circulation for a period of time between 10 to 90 min;

g) Discard and replace the fluid circulating in the system at 37° C.;

h) Collect the target cell culture confined in the central chamber of the device;

i) Extract the molecules originating from the combinatorial library that bound to the target cells;

j) Amplification and reconstitution of the set of molecules extracted from target cells;

k) Identification of candidate molecules for aptamers

INDUSTRIAL APPLICABILITY

In a clinical application, when samples of explants from oncologic patients are co-cultured and arranged in target and non-target, the method can gather the particularities sufficiently necessary for the development of aptamers personalized for that patient. The aptamers developed against cancerous cells of a given patient through the present invention may be used in target anticancer therapies for this patient, acting, for example, as carriers of radiotherapy, chemotherapies, immunotherapies and gene therapies.

REFERENCES

Ahmad, Kareem M., Seung Soo Oh, Seon Kim, Forrest M. McClellen, Yi Xiao, and H. Tom Soh. 2011. "Probing the Limits of Aptamer Affinity with a Microfluidic SELEX Platform." Edited by Maxim Antopolsky. PLoS ONE 6 (11): e27051. https://doi.org/10.1371/journal.pone.0027051.

Beck, Alain, Liliane Goetsch, Charles Dumontet, and Nathalie Corvaïa. 2017. "Strategies and Challenges for the next Generation of Antibody-Drug Conjugates." Nature Reviews Drug Discovery. Nature Publishing Group. https://doi.org/10.1038/nrd.2016.268.

Birch, Christina M., Han Wei Hou, Jongyoon Han, and Jacquin C. Niles. 2015. "Identification of Malaria Parasite-Infected Red Blood Cell Surface Aptamers by Inertial Microfluidic SELEX (I-SELEX)." Sci Rep. 5 (1): 11347. https://doi.org/10.1038/srep11347.

Chen, Dana, Yaron Orenstein, Rada Golodnitsky, Michal Pellach, Dorit Avrahami, Chaim Wachtel, Avital Ovadia-Shochat, et al. 2016. "SELMAP—SELEX Affinity Landscape MAPping of Transcription Factor Binding Sites Using Integrated Microfluidics." Sci Rep. 6 (1): 33351. https://doi.org/10.1038/srep33351.

Cheng, Congsheng, Yong Hong Chen, Kim A. Lennox, Mark A. Behlke, and Beverly L. Davidson. 2013. "In Vivo SELEX for Identification of Brain-Penetrating Aptamers." Mol Ther Nucleic Acids 2 (November 2012): e67. https://doi.org/10.1038/mtna.2012.59.

Cho, M., Y. Xiao, J. Nie, R. Stewart, A. T. Csordas, S. S. Oh, J. A. Thomson, and H. T. Soh. 2010. "Quantitative Selection of DNA Aptamers through Microfluidic Selection and High-Throughput Sequencing." Proc Natl Acad Sci USA. 107 (35): 15373-78. https://doi.org/10.1073/pnas.1009331107.

Civit, Laia, Seyed Mohammad Taghdisi, Anna Jonczyk, Silvana K. Haβel, Carsten Grober, Michael Blank, H. James Stunden, et al. 2018. "Systematic Evaluation of Cell-SELEX Enriched Aptamers Binding to Breast Cancer Cells." Biochimie 145: 53-62. https://doi.org/10.1016/j.biochi.2017.10.007.

Craighead, Harold, G., T. Lis, John, So Youn Kim, and Seungmin Park. 2010. Device for rapid identification of nucleic acids for binding to specific chemical targets. WO2010019969, issued Feb. 18, 2010.

Danke, Xu, Li Hui, Liu Xiaohui, and Chen Zhu. 2018. Method for screening aptamer by using microarray microfluidic chip. WO2018068448, issued 2018. https://worldwide.espacenet.com/publicationDetails/biblio?FT=D&date= 20180419&D B=EPODOC&locale=enEP&CC= WO&NR=2018068448A1&KC=A1&ND=4.

Dassie, Justin P., Xiu Ying Liu, Gregory S. Thomas, Ryan M. Whitaker, Kristina W. Thiel, Katie R. Stockdale, David K. Meyerholz, Anton P. McCaffrey, James O. McNamara, and Paloma H. Giangrande. 2009. "Systemic Administration of Optimized Aptamer-SiRNA Chimeras Promotes Regression of PSMA-Expressing Tumors." Nature Biotechnology 27 (9): 839-46. https://doi.org/10.1038/nbt.1560.

David, Griffiths Andrew, Weitz David, Link Darren Roy, and Bibette Jerome. 2017. Compartmentalised screening by microfluidic control. US2017102381, issued 2017. https://worldwide.espacenet.com/publicationDetails/biblio?DB= EPODOC&II=13&ND=3&adjacent=true&locale=en_ EP&FT=D&date=20170413&CC=US&NR=201710238 1A1&KC=A1.

Eusik, Yoon, Zhang Zhixiong, and Chen Yu Chih. 2018. Systems and methods for high throughput screening. WO2018067802, issued 2018. https://worldwide.espacenet-.com/publicationDetails/biblio?DB=EPODOC&II=4&ND= 3&adjacent=true&locale=en_EP&FT=D&date=20180412 &CC=WO&NR=2018067802 A1&KC=A1.

Gopinathan, Priya, Lien-Yu Hung, Chih-Hung Wang, Nai-Jung Chiang, Yu-Chun Wang, Yan-Shen Shan, and Gwo-Bin Lee. 2017. "Automated Selection of Aptamers against Cholangiocarcinoma Cells on an Integrated Microfluidic Platform." Biomicrofluidics 11 (4): 044101. https://doi.org/10.1063/1.4991005.

Huang, Chao-June, Hsin-I. Lin, Shu-Chu Shiesh, and Gwo-Bin Lee. 2010. "Integrated Microfluidic System for Rapid Screening of CRP Aptamers Utilizing Systematic Evolution of Ligands by Exponential Enrichment (SELEX)." Biosens Bioelectron. 25 (7): 1761-66. https://doi.org/10.1016/j.bios.2009.12.029.

Huang, Chao-Jyun, Hsin-I. Lin, Shu-Chu Shiesh, and Gwo-Bin Lee. 2012. "An Integrated Microfluidic System for Rapid Screening of Alpha-Fetoprotein-Specific Aptamers." Biosens Bioelectron. 35 (1): 50-55. https://doi.org/10.1016/j.bios.2012.02.024.

Hung, Lien-Yu, Chien-Yu Fu, Chih-Hung Wang, Yuan-Jhe Chuang, Yi-Cheng Tsai, Yi-Ling Lo, Pang-Hung Hsu, et al. 2018. "Microfluidic Platforms for Rapid Screening of Cancer Affinity Reagents by Using Tissue Samples." Biomicrofluidics 12 (5): 054108. https://doi.org/10.1063/1.5050451.

Hung, Lien-Yu, Chih-Hung Wang, Yu-Jui Che, Chien-Yu Fu, Hwan-You Chang, Kuan Wang, and Gwo-Bin Lee. 2015. "Screening of Aptamers Specific to Colorectal Cancer Cells and Stem Cells by Utilizing On-Chip Cell-SELEX." Sci Rep. 5 (1): 10326. https://doi.org/10.1038/srep10326.

Hung, Lien Yu, Chih Hung Wang, Keng Fu Hsu, Cheng Yang Chou, and Gwo Bin Lee. 2014. "An On-Chip Cell-SELEX Process for Automatic Selection of High-Affinity Aptamers Specific to Different Histologically Classified Ovarian Cancer Cells." Lab on a Chip 14 (20): 4017-28.https://doi.org/10.1039/c41c00587b.

Hybarger, Glen, Joseph Bynum, Robert F. Williams, James J. Valdes, and James P. Chambers. 2006. "A Microfluidic SELEX Prototype." Anal Bioanal Chem. 384 (1): 191-98. https://doi.org/10.1007/s00216-005-0089-3.

Kim, Jinho, Timothy R. Olsen, Jing Zhu, John P. Hilton, Kyung-Ae Yang, Renjun Pei, Milan N. Stojanovic, and Qiao Lin. 2016. "Integrated Microfluidic Isolation of Aptamers Using Electrophoretic Oligonucleotide Manipulation." Sci Rep. 6 (1): 26139. https://doi.org/10.1038/srep26139.

Lai, Hsien-Chih, Chih-Hung Wang, Tong-Miin Liou, and Gwo-Bin Lee. 2014. "Influenza A Virus-Specific Aptamers Screened by Using an Integrated Microfluidic System." Lab Chip. 14 (12): 2002-13. https://doi.org/10.1039/c41c00187g.

Lin, Hsin-I, Ching-Chu Wu, Ching-Hsuan Yang, Ko-Wei Chang, Gwo-Bin Lee, and Shu-Chu Shiesh. 2015. "Selection of Aptamers Specific for Glycated Hemoglobin and Total Hemoglobin Using On-Chip SELEX." Lab Chip 15 (2): 486-94. https://doi.org/10.1039/c41c01124d.

Liu, Haoran, Junhua Mai, Jianliang Shen, Joy Wolfram, Zhaoqi Li, Guodong Zhang, Rong Xu, et al. 2018. "A Novel DNA Aptamer for Dual Targeting of Polymorphonuclear Myeloid-Derived Suppressor Cells and Tumor Cells." Theranostics 8 (1): 31-44. https://doi.org/10.7150/thno.21342.

Liu, Xiaohui, Hui Li, Wenchao Jia, Zhu Chen, and Danke Xu. 2016. "Selection of Aptamers Based on a Protein Microarray Integrated with a Microfluidic Chip." Lab Chip. 17 (1): 178-85. https://doi.org/10.1039/c61c01208f.

Lou, X., J. Qian, Y. Xiao, L. Viel, A. E. Gerdon, E. T. Lagally, P. Atzberger, T. M. Tarasow, A. J. Heeger, and H. T. Soh. 2009. "Micromagnetic Selection of Aptamers in Microfluidic Channels." Proc Natl Acad Sci USA. 106 (9): 2989-94. https://doi.org/10.1073/pnas.0813135106.

Mayer, Gunter. 2009. "The Chemical Biology of Aptamers." Angew Chem Int Ed Engl. 48 (15): 2672-89. https://doi.org/10.1002/anie.200804643.

Mi, Jing, Yingmiao Liu, Zahid N. Rabbani, Zhongguang Yang, Johannes H. Urban, Bruce A. Sullenger, and Bryan M. Clary. 2010. "In Vivo Selection of Tumor-Targeting RNA Motifs." Nat Chem Biol. 6 (1): 22-24. https://doi.org/10.1038/nchembio.277.

Mi, Jing, Partha Ray, Jenny Liu, Chien Tsun Kuan, Jennifer Xu, David Hsu, Bruce A. Sullenger, Rebekah R. White, and Bryan M. Clary. 2016. "In Vivo Selection Against Human Colorectal Cancer Xenografts Identifies an Aptamer That Targets RNA Helicase Protein DHX9." Mol Ther Nucleic Acids 5 (October 2015): e315. https://doi.org/10.1038/mtna.2016.27.

Oh, Seung Soo, Kareem M. Ahmad, Minseon Cho, Seon Kim, Yi Xiao, and H. Tom Soh. 2011. "Improving Aptamer Selection Efficiency through Volume Dilution, Magnetic Concentration, and Continuous Washing in Microfluidic Channels." Anal Chem. 83 (17): 6883-89. https://doi.org/10.1021/ac201269f.

Olsen, Timothy, Jing Zhu, Jinho Kim, Renjun Pei, Milan N Stojanovic, and Qiao Lin. 2017. "An Integrated Microfluidic SELEX Approach Using Combined Electrokinetic and Hydrodynamic Manipulation." SLAS Technol. 22 (1): 63-72. https://doi.org/10.1177/2211068216659255.

Park, Jee-Woong, Su Jin Lee, Shuo Ren, Sangwook Lee, Soyoun Kim, and Thomas Laurell. 2016. "Acousto-Microfluidics for Screening of SsDNA Aptamer." Sci Rep. 6 (1): 27121. https://doi.org/10.1038/srep27121.

Park, Seung-min, Ji-Young Ahn, Minjoung Jo, Dong-ki Lee, John T. Lis, Harold G. Craighead, and Soyoun Kim. 2009. "Selection and Elution of Aptamers Using Nanoporous Sol-Gel Arrays with Integrated Microheaters." Lab Chip. 9 (9): 1206. https://doi.org/10.1039/b814993c.

Qian, Jiangrong, Xinhui Lou, Yanting Zhang, Yi Xiao, and H. Tom Soh. 2009. "Generation of Highly Specific Aptamers via Micromagnetic Selection." Anal. Chem. 81 (13): 5490-95. https://doi.org/10.1021/ac900759k.

Sinha, Anirban, Priya Gopinathan, Yi-Da Chung, Hsin-Ying Lin, Kuang-Hsien Li, Hsi-Pin Ma, Po-Chiun Huang, Shu-Chu Shiesh, and Gwo-Bin Lee. 2018. "An Integrated Microfluidic Platform to Perform Uninterrupted SELEX Cycles to Screen Affinity Reagents Specific to Cardiovascular Biomarkers." Biosens Bioelectron. 122 (December): 104-12. https://doi.org/10.1016/j.bios.2018.09.040.

So, Youn Kim, Ji-Young Ahn Minjoung, and Kyung Kim Tae. 2012. Multiplex microfluidic device for selecting nucleic acid aptamers, and high throughput selection method for nucleic acid aptamers using same. CN102639720, issued 2012. https://worldwide.espacenet.com/publicationDetails/biblio?DB=EPODOC&II=2&ND=3&adjacent=true&locale=en_EP&FT=D&date=20120815&CC=CN&NR=102639720A &KC=A.

Stoll, Heidi, Heiko Kiessling, Martin Stelzle, Hans Peter Wendel, Julia Schütte, Britta Hagmeyer, and Meltem Avci-Adali. 2015. "Microfluidic Chip System for the Selection and Enrichment of Cell Binding Aptamers." Biomicrofluidics 9 (3): 034111. https://doi.org/10.1063/1.4922544.

Tuerk, C, and Larry Gold. 1990. "Selection of RNA Molecules That Bind to T4 DNA-Polymerase." Science 249: 505-510.

Wang, Hanlu, Yibang Zhang, Haiping Yang, Meng Qin, Xinxin Ding, Rihe Liu, and Yongping Jiang. 2018. "In Vivo SELEX of an Inhibitory NSCLC-Specific RNA Aptamer from PEGylated RNA Library." Mol Ther Nucleic Acids 10 (March): 187-98. https://doi.org/10.1016/j.omtn.2017.12.003.

Wang, Qing, Wei Liu, Yuqian Xing, Xiaohai Yang, Kemin Wang, Rui Jiang, Pei Wang, and Qing Zhao. 2014. "Screening of DNA Aptamers against Myoglobin Using a Positive and Negative Selection Units Integrated Microfluidic Chip and Its Biosensing Application." Anal Chem. 86 (13): 6572-79. https://doi.org/10.1021/ac501088q.

Weng, Chen-Hsun, I-Shan Hsieh, Lien-Yu Hung, Hsin-I Lin, Shu-Chu Shiesh, Yuh-Ling Chen, and Gwo-Bin Lee. 2013. "An Automatic Microfluidic System for Rapid Screening of Cancer Stem-like Cell-Specific Aptamers." Microfluid Nanofluidics. 14 (3-4): 753-65. https://doi.org/10.1007/s10404-012-1095-3.

Yang, Xiaohai, Qing Wang, Kemin Wang, Yugian Xink, and Rui Jiang. 2012. Nucleic acid aptamer capable of detecting myohemoglobin, microfluidic chip for screening and screening method and application. CN102703454, issued 2012. https://worldwide.espacenet.com/publication-Details/biblio?DB=EPODOC&II=1&ND=3&adjacent=true&locale=en_EP&FT=D&date=20121003&CC=CN&NR=102703454A &KC=A.

Yasuda, Kenji, Hideyuki Terazono, Kentetsu Kin, Masahito Hayashi, and Akihiro Hattori. 2011. Selection method for nucleic acid specifically bonding to target molecule of target cell surface. JP2012196197A, issued May 13, 2011.

Ye, Mao, Jun Hu, Minyuan Peng, Jing Liu, Jun Liu, Huixia Liu, Xielan Zhao, and Weihong Tan. 2012. "Generating Aptamers by Cell-SELEX for Applications in Molecular Medicine." Int J Mol Sci. 13 (3): 3341-53. https://doi.org/10.3390/ijms13033341.

The invention claimed is:

1. A method for selecting aptamers with target cell binding specificity in a microfluidic device platform for co-culture of multiple cell cultures, the method comprising co-culturing cancerous target cells and non-cancerous non-target cells explanted from patients in an arrangement of microfluidic devices, wherein the co-culturing of the cancerous target cells and the non-cancerous non-target cells is carried out in a closed modular arrangement system with fluid circulation guided by combinations of microfluidic devices connected in parallel, in series, or a combination thereof; and wherein a step of injecting an aptamer combinatorial library in said closed system is carried out after a homeostatic balance has been established between the cancerous target cells and the non-cancerous non-target cells, and fluid components circulating through the closed system.

2. The method for selecting aptamers according to claim 1, wherein the method comprises the following steps:

(a) fixing in a central chamber of a microfluidic device substrate a support containing and appropriate porosity insert for the confinement of cell types of interest;

(b) arranging the microfluidic devices modularly in a closed system through combination connections in series, in parallel, or a combination thereof through coupling of protuberances of the substrate to connectors and to silicone tubes;

(c) filing a system of channels and chambers of the microfluidic devices with fluid;

(d) accommodating cell cultures of interest in the central chamber of the microfluidic devices;

(e) circulating the fluid in the system channels and chambers for an adequate period of time;

(f) injecting a combinatorial library of molecules into the system and circulating the combinatorial library of molecules for a period of time;

(g) removing and replacing the fluid circulating in the system;

(h) collecting a target cell culture confined in the central chamber of the microfluidic device, (i) extracting molecules originating from the combinatorial library of molecules that bound to target cells in the target cell culture;

(j) amplifying and reconstituting the set of molecules extracted from the target cells; and (k) identifying candidate molecules for aptamers.

3. The method for selecting aptamers according to claim 2, wherein step (c) occurs at 37° C.

4. The method for selecting aptamers according to claim 2, wherein the appropriate time in step (e) is from 10 to 72 hours.

5. The method for selecting aptamers according to claim 2, wherein the period of time in step (f) is from 10 to 90 min.

6. The method for selecting aptamers according to claim 2, wherein step (g) occurs at 37° C.

* * * * *